US008431625B2

(12) United States Patent
Luchterhandt et al.

(10) Patent No.: US 8,431,625 B2
(45) Date of Patent: Apr. 30, 2013

(54) COMPOSITIONS CURABLE BY RING OPENING METATHESIS POLYMERIZATION AT LOW TEMPERATURES AND THEIR APPLICATION IN THE DENTAL FIELD

(75) Inventors: Thomas Luchterhandt, Greifenberg (DE); Peter Bissinger, Diessen (DE); Miriam Hansen, München (DE)

(73) Assignee: 3M Innovative Properties Company, St. Paul, MN (US)

( * ) Notice: Subject to any disclaimer, the term of this patent is extended or adjusted under 35 U.S.C. 154(b) by 734 days.

(21) Appl. No.: 12/517,727

(22) PCT Filed: Dec. 18, 2007

(86) PCT No.: PCT/US2007/087841
§ 371 (c)(1),
(2), (4) Date: Jun. 4, 2009

(87) PCT Pub. No.: WO2008/077001
PCT Pub. Date: Jun. 26, 2008

(65) Prior Publication Data
US 2010/0036015 A1    Feb. 11, 2010

(30) Foreign Application Priority Data
Dec. 20, 2006  (EP) .................................... 06026426

(51) Int. Cl.
*A61K 6/093* (2006.01)
(52) U.S. Cl.
USPC ........................................................ 523/115
(58) Field of Classification Search .................. None
See application file for complete search history.

(56) References Cited

U.S. PATENT DOCUMENTS

| | | | |
|---|---|---|---|
| 5,854,299 A | 12/1998 | Mühlebach et al. | |
| 5,861,443 A | 1/1999 | Hafner et al. | |
| 5,973,085 A | 10/1999 | Mühlebach et al. | |
| 6,001,909 A | 12/1999 | Setiabudi | |
| 6,075,068 A | 6/2000 | Bissinger | |
| 6,844,409 B2 | 1/2005 | Angeletakis | |
| 7,001,590 B1 | 2/2006 | Angeletakis | |
| 7,691,919 B2 | 4/2010 | Smolak et al. | |
| 2002/0153096 A1 | 10/2002 | Giardello | |
| 2002/0185630 A1 | 12/2002 | Piccinelli et al. | |
| 2003/0212233 A1* | 11/2003 | Angeletakis et al. | 528/15 |
| 2003/0220512 A1 | 11/2003 | Blechert | |
| 2004/0225073 A1* | 11/2004 | Angeletakis | 525/342 |
| 2004/0254320 A1 | 12/2004 | Angeletakis | |
| 2005/0015951 A1 | 1/2005 | Strebe | |
| 2005/0159510 A1 | 7/2005 | Smolak et al. | |
| 2006/0004158 A1 | 1/2006 | Moszner et al. | |
| 2006/0241257 A1 | 10/2006 | Angeletakis | |
| 2009/0088494 A1 | 4/2009 | Luchterhandt et al. | |
| 2010/0036015 A1 | 2/2010 | Luchterhandt et al. | |

FOREIGN PATENT DOCUMENTS

| | | |
|---|---|---|
| CA | 2051333 | 3/1992 |
| CA | 2297442 A1 | 8/2000 |
| CA | 10 335 417 A | 2/2005 |
| DE | 4029230 | 9/1990 |
| EP | 771830 | 5/1997 |
| EP | 1317914 | 6/2000 |
| EP | 1025830 A2 | 8/2000 |
| EP | 1614410 | 1/2006 |
| EP | 1656924 | 5/2006 |
| JP | 63-128063 | 5/1988 |
| JP | 63-128065 | 5/1988 |
| JP | 2001 003028 | 1/2001 |
| JP | 2001-003028 * | 1/2001 |
| JP | 17-200652 | 7/2005 |
| WO | WO 95/07310 | 3/1995 |
| WO | WO 96/16008 A1 | 5/1996 |
| WO | WO 96/16103 | 5/1996 |
| WO | WO 97/32913 A1 | 9/1997 |
| WO | WO 00/46257 | 8/2000 |
| WO | WO 02/14376 A | 2/2002 |
| WO | WO 03/093351 A1 | 11/2003 |
| WO | WO 2004/035596 A | 4/2004 |
| WO | WO 2004/101685 | 11/2004 |
| WO | WO 2005/053843 A | 6/2005 |

OTHER PUBLICATIONS

Machine translation of JP-2001-003028.*
McCabe et al., 1991, *British Dental Journal* 171:246-248 "Mechanical Properties of a Composite Inlay Material Following Post-Curing".
Krause, et al., "Heterogenization of a Modified Grubbs-Hoveyda Catalyst on a ROMP-Derived Monolithic Support", Macromol. Rapid Commun, vol. 24, No. 15, pp. 875-878, (2003).
Andres Baltzer and Vanik Kaufmann-Jinoian, *Quintessenz Zahntechnik*, 30, 7, 726-740 (2004).
Castarlenas, R et al., *Journal of Organometallic Chemistr*; 663 (2002) 235-238.
Dexter et al., in *Encyclopedia of Polymer Science and Technology*, "Acoustic Properties to Cyclopentadiene and Dicyclopentadiene", Copyright © 2002, by John Wiley & Sons, Inc.; vol. 5, 164-183.
Hafner, A. et al (CIBA SC) *Angew. Chem. Int.*, "One-Component Catalysts for Thermal and Photoinduced Ring Opening Matathesis Polymerization", Ed. 36 (1997) 2121-2124.

(Continued)

*Primary Examiner* — Randy Gulakowski
*Assistant Examiner* — Jeffrey Washville
(74) *Attorney, Agent, or Firm* — Pamela L. Stewart; Stephen L. Crooks

(57) ABSTRACT

The invention relates to a composition which is polymerizable by ring-opening metathesis polymerization (ROMP) comprising at least one monomer that is polymerizable by ROMP, at least one initiator of the Hoveyda-Grubbs type for initiating the ROMP and at least one retarder selected from the group consisting of heterocyclic a means having a ring with at least one N-atom and four or less other atoms constituting the ring bearing the at least one N-atom. The invention further relates to a process for the preparation of a composition which is polymerizable by ROMP, a dental material obtainable by polymerizing a composition according to the invention and the use of a substance selected from the group consisting of heterocyclic amines having a ring with at least one N-atom and five or less atoms constituting the ring bearing the at least one N-atom or of a mixture of two or more of such substances as a retarder in ROMP.

15 Claims, 1 Drawing Sheet

OTHER PUBLICATIONS

Matos et al., *Journal of Molecular Catalysis A: Chemical 222*, "Piperidine as ancillary ligand in the novel [RuCl$_2$(PPh$_3$)$_2$(piperidine)] complex for metathesis polymerization of norbornene and norbornadiene", (2004) 81-85.

Slugovc et al., "Ring opening metathesis polymerisation in donor solvents", ChemCommun 2002, 2572-2573.

Vygodskii et al., *Macromolecules*, Ring-Opening Metathesis Polymerization (ROMP) in Ionic Liquids: Scope and Limitations, 2006, 39, 7821-7830.

XP-002434083, Weskamp et al., "Hochaktive Rutheniumkatalysatoren für die Olenfinmetathese: die Synergie N-hererocyclischer Carbene and koordinativ labiler Lindanden", Agnew: Chem 1999, vol. 111, Nr. 16, 2573-2576.

Search and Examination of EP Application No. 06002150; 7 pgs.

ISO/ISA for PCT/US2007/002576; 13pgs.

Search and Examination of EP Application No. 06026426, 8 pgs.

ISO/ISA for PCT/US2007/087841; 15 pgs.

\* cited by examiner

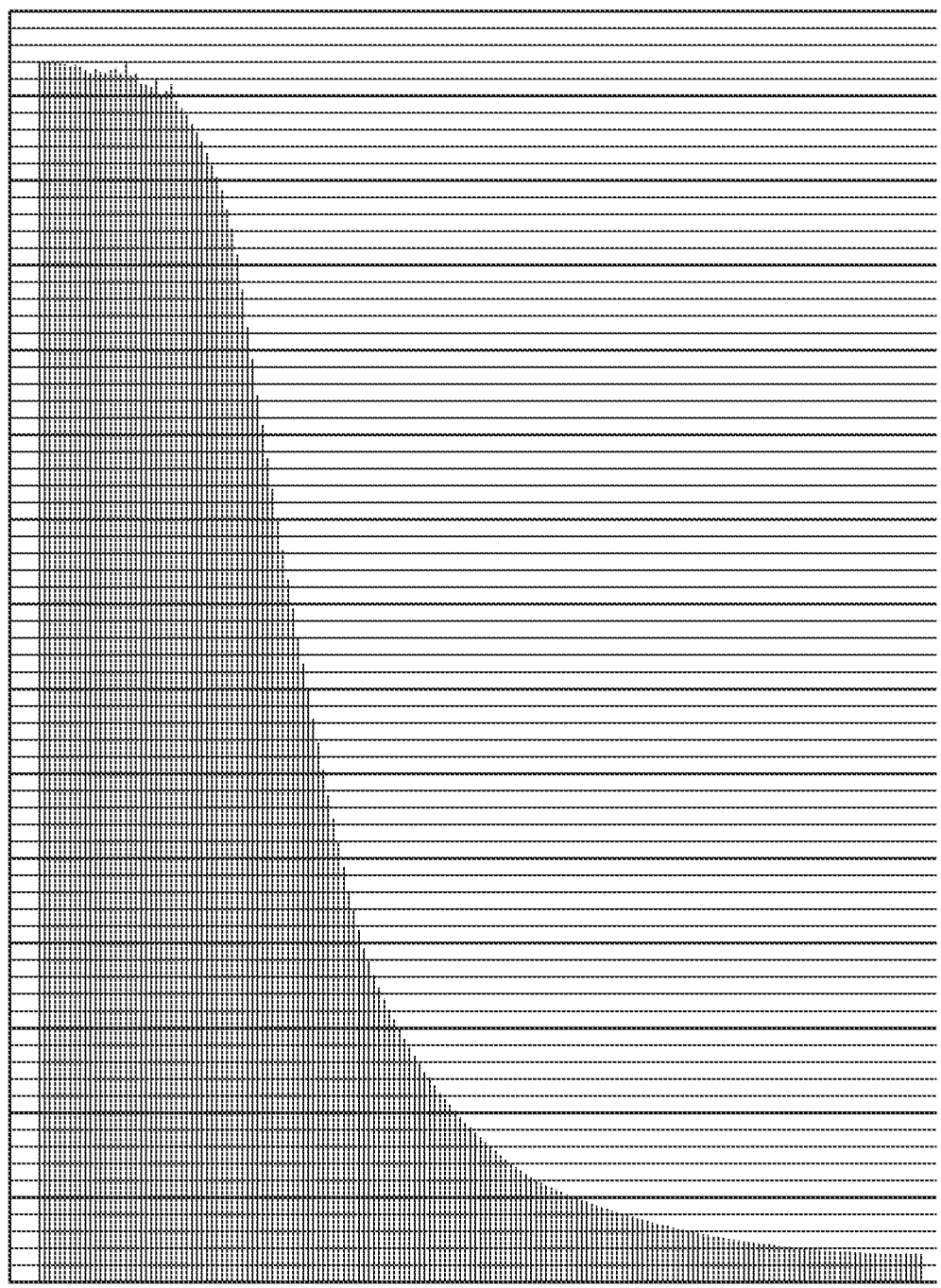
$t_A$=2.8 min, Past 1R

COMPOSITIONS CURABLE BY RING OPENING METATHESIS POLYMERIZATION AT LOW TEMPERATURES AND THEIR APPLICATION IN THE DENTAL FIELD

CROSS-REFERENCE TO RELATED APPLICATION

This application is a national stage filing under 35 U.S.C. 371 of PCT/US2007/087841, filed Dec. 18, 2007, which claims priority to European Application No.06026426.4, filed Dec. 10, 2006, the disclosure of which is incorporated by reference in its/their entirety herein

BACKGROUND

The invention relates to a composition which is polymerizable by ring-opening metathesis polymerization (ROMP) comprising at least one monomer that is polymerizable by ROMP, at least one initiator of the Hoveyda-Grubbs type for initiating the ROMP and at least one retarder selected from the group consisting of heterocyclic amines having a ring with at least one N-atom and five or less atoms constituting the ring bearing the at least one N-atom. The invention further relates to a process for the preparation of a composition which is polymerizable by ROMP, a dental material obtainable by polymerizing a composition according to the invention and the use of a substance selected from the group consisting of heterocyclic amines having a ring with at least one N-atom and five or less atoms constituting the ring bearing the at least one N-atom or of a mixture of two or more of such substances as a retarder in ROMP.

Addition polymerizing reactions have been widely used in the field of dental applications. Mostly silicon resins have been utilized and have been cured, often as a two-part system via hydrosilylation reaction. An advantage of such systems is their flexible working time which, depending on the requirements, can be adjusted broadly within a range of from less than about one minute up to several hours. The working time can generally be controlled via the components present in the composition to be polymerized or by specifically adding retarders or inhibitors to the catalyst component.

Due to reasons which have, e.g., been mentioned in the prior art (see, e.g., U.S. Pat. No. 6,844,409 B2) addition polymerizable systems have many shortcomings. In order to remedy some of those shortcomings, another type of polymerization system has been developed where curing is achieved by a ring-opening metathesis polymerization (ROMP).

According to a definition given in U.S. Pat. No. 6,844,409 B2, metathesis is often understood to mean the metal catalyzed redistribution of carbon-carbon double bonds. A ROMP polymerizable composition generally can comprise a resin system that includes functionalities or groups that are curable by ROMP together with a metathesis catalyst such as a Ruthenium carbene complex.

U.S. Pat. No. 6,844,409 B2 relates to a composition curable by metathesis reaction comprising an olefin-containing resin system and metathesis catalyst. The metathesis is initiated by a Ruthenium carbene complex catalyst which is increased in activity by either an activity enhancing ligand or by incorporation of a catalyst accelerator into the described resin formulation. As catalyst accelerators sulfosuccinate salts are described. Retardation of the ROMP-reaction is not mentioned in the document.

Slugovc, Demel and Stelzer describe in ChemCommun 2002, 2572-2573 the influence of N-substituted compounds on ROMP polymerization with a so-called super-Grubbs catalyst. The use of functional group bearing additives in large amounts and the influence of such additives on the polymerization behaviour is described. While generally effects of slowing down the polymerization and a large influence on the polymer properties is described, neither a tailored retardation of the polymerization reaction or the absence of a significant influence on the mechanical properties of the obtained polymer are described in the document.

Matos and Lima-Neto Journal of molecular catalysis A: chemical 222 (2004) 81-85 describe the formation of a ruthenium complex which quantitatively polymerizes norbornene via ROMP in less than one minute at RT. While a decrease of catalyst activity upon the addition of ethyldiazoacetate is observed, the phenomenon of retardation, leaving the general polymerization mechanism basically unchanged is not described in the document.

US 2004/0225073 A1 describes a composition curable by a metathesis reaction upon mixing its components, which comprises an olefin-containing substrate, a metathesis catalyst and a reaction control agent for doing the progress of the metathesis reaction. The reaction control agent is an organic compound that contains carbon-carbon double and/or triple bonds and one or more Group 14 atoms and is present in an amount effective to slow the progress of the metathesis reaction. The document also describes the use of pyridine, triethylamin and benzotriazole as comparative retarders.

Upon comparing the retardation properties of these compounds, the document comes to the conclusion that they either accelerate the curing process (triethylamin), suppress the curing reaction (benzotriazole) or have no effect at all (pyridine).

US 2002/0153096 A1 relates to an adhesion agent composition comprising at least one olefin compound having at least one metathesis active double bond, wherein the olefin is substituted or unsubstituted and at least one compatibilising functionality for interacting with the substrate surface. A retarder which does not become part of the polymer is not mentioned in the document.

U.S. Pat. No. 6,001,909 relates to a composition comprising at least one tight cyclo olefin, a catalyst for the ring opening metathesis polymerization, a filler and a silane. The silanes are added in order to increase toughness, heat stability and dielectric loss factor of ROMP-polymerized systems. The silanes can carry substituents and are used in an amount of from 0.01 to 20% by weight in relation to the weight to the composition. Curing is achieved by heating the sample for 2 hours to 80° C., 4 hours to 100° C. and 1 hour to 150° C.

Yakov S. Vygodskii et al deal with the scope and limitations of Ring-Opening Metathesis Polymerization (ROMP) in ionic liquids (Macromolecules 2006, 39, 7821-7830).

US 2006/0241257 A1 describes metathesis-curable composition with a reaction control agent. In the examples tetra allyl silane (TAS) is used as reaction control agent.

Due to the shortcomings of the systems described in the prior art, there was a need for improved compositions which are curable by ROMP, especially for compositions which can be used in the dental field.

SUMMARY OF THE INVENTION

The present invention provides a composition which is polymerizable by ring-opening metathesis polymerization (ROMP) comprising at least one monomer that is polymerizable by ROMP, at least one initiator of the Hoveyda-Grubbs type for initiating the ROMP and at least one retarder selected from the group consisting of heterocyclic amines having a ring with at least one N-atom and five or less atoms constituting the ring bearing at least one N-atom. In some instance it has been found to be advantageous, if the retarder is able to form a complex with Ruthenium.

According to another aspect of the invention a process for the preparation of a composition which is polymerizable by ring-opening metathesis polymerization (ROMP) is described, wherein at least one monomer that is polymerizable by ROMP and at least one initiator of the Hoveyda-Grubbs type for initiating the ROMP and at least one retarder selected from the group consisting of heterocyclic amines having a ring with at least one N-atom and five or less atoms constituting the ring bearing the at least one N-atom, are mixed. It has under certain circumstances been found to be advantageous if the composition described according to the invention is present as a base component and a catalyst component, wherein the base component at least comprises one or more monomers polymerizable by ROMP and the catalyst component at least comprises at least one initiator of the Hoveyda-Grubbs type for initiating a ROMP and the retarder is present in the base component or the catalyst component or in both.

In a further aspect of the invention a dental material obtainable by polymerizing a composition according to the invention or by polymerizing a composition obtainable according to a process as described according to the invention is described.

Furthermore, the invention relates to the use of a substance selected from the group consisting of heterocyclic amines having a ring with at least N-atom and five or less atoms constituting the ring bearing the at least one N-atom or of a mixture of two or more of such substances as a retarder in ROMP.

Moreover, the use of a material obtainable by polymerizing a composition according to the invention or by polymerizing a composition obtainable according to a process as described in the invention for the preparation of temporary or permanent inlays, onlays, veneer shells, crowns, or bridges, or filling materials is described.

Using the retarders described in the text of the invention, it has been found that these retarders do not only facilitate a delay of the curing process of the curable composition but also allow for providing a composition with a tooth-coloured appearance or a composition, the colour of which can be adjusted to a tooth-coloured appearance by adding colourants or pigments.

Moreover, with respect to certain embodiments it was found that a ROMP-curable composition containing a retarder described in the text of the present invention, shows improved physical properties, such as flexural strength, after hardening.

Without wishing to be bound to this or another theory, it is believed that due to the delay in the curing process, the curable monomers in the composition have more time to react with each other, having the result that the hardening or crosslinking reaction is more effective. This might lead to improved physical properties.

DESCRIPTION OF THE DRAWINGS

FIG. 1 shows a relevant fragment of the curing behaviour of paste 1R (described in the Examples Section below) measured with a curometer. The x-axis indicates the time and the y-axis the viscosity, with a high viscosity at the lower end and a low viscosity at the upper end. When the upper plateau of the graph is dropping by at least two squares, it is considered that the curing reaction has started. The length of two squares represents one minute, meaning, that $1/10^{th}$ of a square equals 3 s.

DETAILED DESCRIPTION OF THE INVENTION

According to a first aspect, the invention relates to a composition which is polymerizable by ring-opening metathesis polymerization (ROMP) comprising
a) at least one monomer that is polymerizable by ROMP,
b) at least one initiator of the Hoveyda-Grubbs type for initiating the ROMP and
c) at least one retarder selected from the group consisting of heterocyclic amines having a ring with at least one N-atom and 5, 4 or less atoms constituting the ring bearing the at least one N-atom.

The polymerizable composition preferably can comprise at least one monomer that is polymerizable by ROMP with a fraction of at least about 1% by weight. The amount of monomer that has two or more moieties polymerizable by ROMP can be higher, e.g., at least about 10, about 20, about 30, about 40, about 50 or about 60% by weight of the monomers in the composition or even higher, e.g., more than about 70, more than about 80, or even about 90% by weight.

In another embodiment, a composition according to the invention contains a monomer which is polymerizable by ROMP and comprises at least one C—C double bond in a cyclic structure.

Generally, all types of monomers can be part of the composition which have one moiety or preferably two or more moieties that can be polymerized by ROMP.

Generally, suitable monomers can follow the general formula B-$A_n$, wherein A is a moiety polymerizable by ROMP, e.g. cyclobutenyl, cyclopentenyl, cyclooctenyl or bicyclic ring systems like the often preferred norbornenyl and 7-oxanorbornenyl groups, B is an organic or silicon-organic backbone with 1 to about 100, e.g., 1 to about 10 or 1 to about 5 or 1 to about 4 moieties polymerizable by ROMP, e.g., 1, 2 or 3 moieties polymerizable by ROMP, are attached, n being about 1 to about 100. The composition according to the invention can contain only one type of monomers according to the general formula B-$A_n$. It is also possible that a composition according to the invention contains two or more different types of monomers according to the general formula B-$A_n$. The composition according to the invention preferably contains at least one type of monomer according to the general formula B-$A_n$, which has one or preferably two olefinically unsaturated double bonds which are curable by ROMP.

In a further embodiment, the bicyclic ring systems which can be used according to the invention have no exocyclic C—C double bonds like (meth)acrylate groups so that the curing of the compositions takes place at least predominantly by ring-opening metathesis polymerization (ROMP). Furthermore, in some instances it can be advantageous if the composition and especially the bicyclic ring system also does not contain terminal unsaturation especially vinyl or allyl groups as these sometimes may function as a chain-terminating agent during ROMP. Despite that, however, addition of chain terminating agents in order to regulate polymerization can be preferred.

The compositions according to the invention can contain bicyclic ring systems with 1 to endocyclic double bond. Carbocyclic ring systems are particularly preferred as well as oxygen-substituted ring systems.

Carbocyclic and heterocyclic bicyclo[x.y.z.] hydrocarbons with noticeable ring strain may often be particularly suitable, when x, y and z have values from 1 to 6. x is equal to about 2, y is equal to about 2 and z equal to 1.

Preferred representatives of this composition class are derivatives of bicyclo[2.2.1]heptene or 7-Oxa-bicyclo[2.2.1]heptene in particular those with unsaturation in 5-position and substitution in 2- or 2,3-position to the ring. Substituents in 2- or 2,3-position to the ring are preferably carbon- silicon- or oxygen-functional and connect to an unreactive residue or to an organic or metalorganic spacer bridging between two, three, four or more ROMP-polymerizable groups.

Preferred representatives of this composition class are bicyclo[2.2.1]heptene derivatives and 7-Oxa-bicyclo[2.2.1]heptene derivatives, in particular those according to the following formulae,

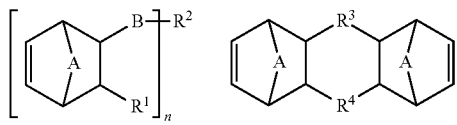

in which n, A, B, $R^1$, $R^2$, $R^3$ and $R^4$ independently from each other, have the following meanings:

A=—$CH_2$— or —O—;

$R^1$=—H; $C_1$ to $C_{12}$ alkyl, aryl or benzyl, preferably $C_1$ to $C_{12}$ alkyl, phenyl or benzyl, in particular methyl, ethyl, propyl butyl, hexyl, octyl, decyl, dodecyl, phenyl, benzyl; —C(=O)—$OR^5$; —O—C(=O)—$R^5$; —$CH_2$—O—C(=O)—$R^5$; $R^5$ standing for —H, $C_1$ to $C_{12}$ alkyl, aryl or benzyl, preferably $C_1$ to $C_{12}$ alkyl, phenyl or benzyl, in particular methyl, ethyl, propyl butyl, hexyl, octyl, decyl, dodecyl, phenyl, benzyl;

B=—O—, —$CH_2$—, —$CH_2$—O—, —$CH_2$—O—($CH_2$—$CH_2$—O)$_m$— (with m=1,2,3,4 or 5), —C(=O)—, —C(=O)—O—, —C(=)O—($CH_2CH_2$—O)$_m$— or is absent;

n=an integer from 1 to 6, preferably 1 to 4, especially 1 to 3;

$R^2$=n-times substituted organic or metalorganic residue $C_1$ to $C_{50}$ that can contain O, N and Si atoms, preferably $C_1$ to $C_{12}$ alkylene, $C_6$ to $C_{24}$ arylene, preferably bisphenol type or tricyclodecane type backbones, biphenylenes, phenylene or naphthylene, discrete siloxanes or carbosilanes, for n=2 $R^2$ can also be a single bond;

$R^3$, $R^4$=a single bond or $C_1$ to $C_{20}$ alkylene, preferably $C_1$ to $C_{12}$ alkylene, in particular $C_1$ to $C_3$ alkylene; a chemical bond, —O— or $R^4$ and $R^{4'}$ together form a >CH—$CH_2$—CH< radical;

as well as stereoisomeric compounds and any mixtures of these substances.

The radicals B, $R^1$, $R^2$, $R^3$ and $R^4$ can be bound in the endo- or exo position. Typically the bicyclic compounds according to the above formulae are present in the form of stereoisomeric mixtures, in particular as racemates.

Preferred compounds are often accordingly those in which at least one of the variables of the formulae has a preferred definition as described above. Also preferred can be those compounds in which several or all of the variables correspond to the preferred definitions.

Quite particularly preferred bicyclic ring systems are bicyclo[2.2.1]hept-2-en (norbornene), 7-oxa-bicyclo[2.2.1]hept-2-ene (7-oxa-norbornene) and substituted derivatives derived therefrom such as esters of bicyclo[2.2.1]hept-5-en-2-carboxylic acid or esters of bicyclo[2.2.1]hept-5-en-2,3-dicarboxylic acid, both with mono-, di- or multifunctional alcohols, esters of bicyclo[2.2.1]hept-5-en-2-ol or bicyclo[2.2.1]hept-5-en-2-methanol or bicyclo[2.2.1]hept-5-en-2-(methyloxy-(2-hydroxy)ethan with mono-, di- and multi carboxylic acids or the reaction products of the mentioned bicyclic alcohols with mono- or diisocyanates.

Respective structural formulae for suitable bicyclic ring systems are given below. The formulae also represent the corresponding position isomers which result from the exchange of substituents $R^1$, $R^2$ and $R^3$, with —R—=—($CH_2$)$_n$—, wherein n is equal to 1 to and wherein the ring may contain O and N.

Useful monomers are given in the lists below:
Monomerlist 1

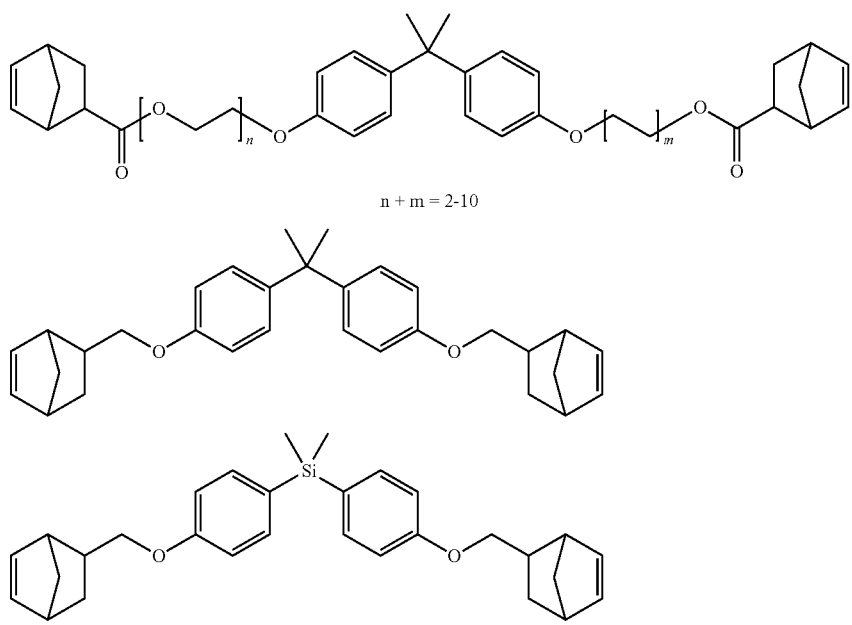

n + m = 2-10

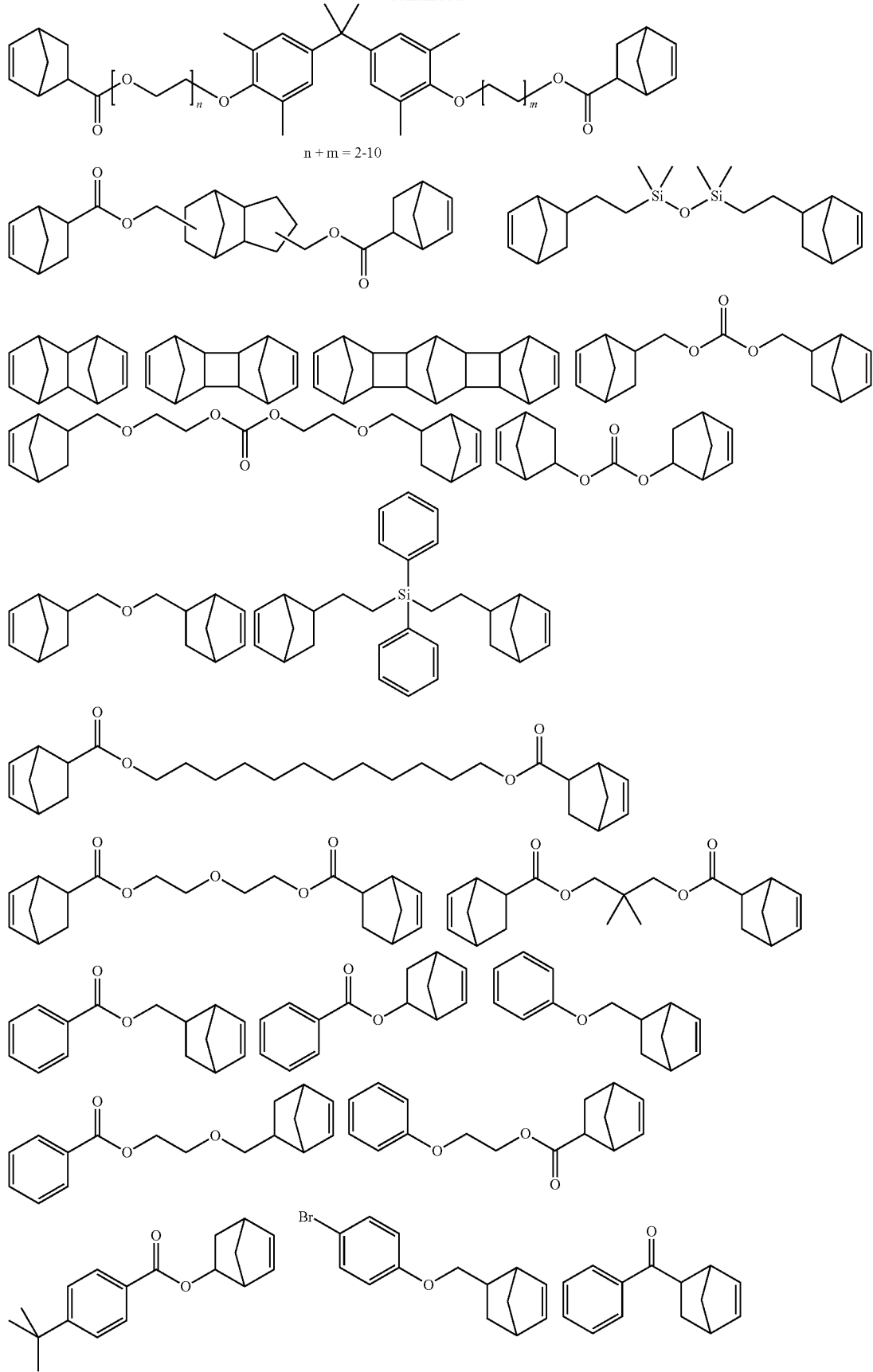

-continued
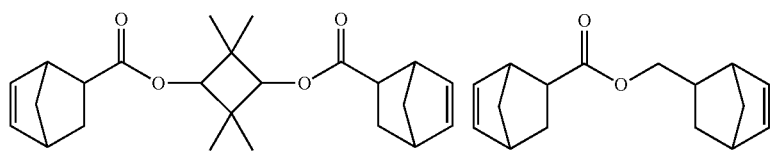
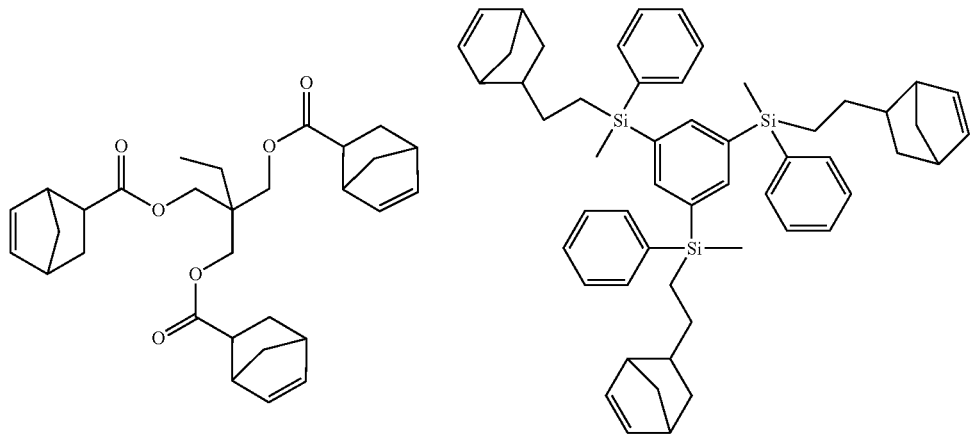
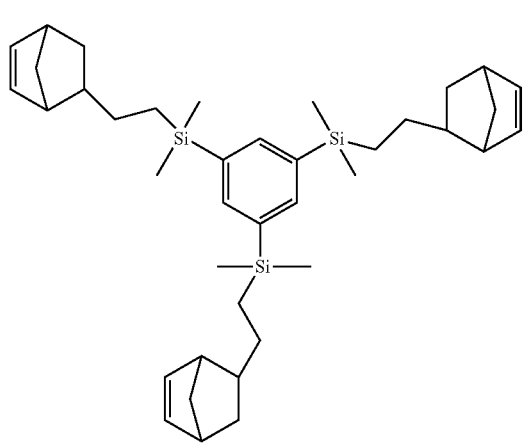
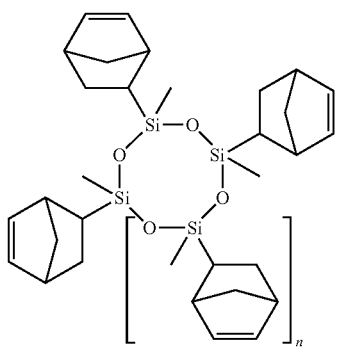
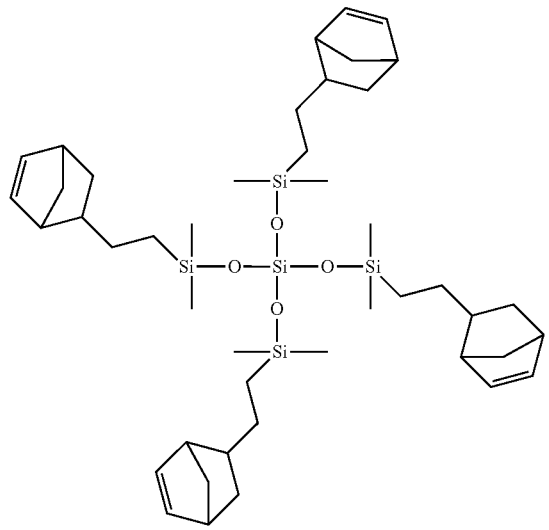
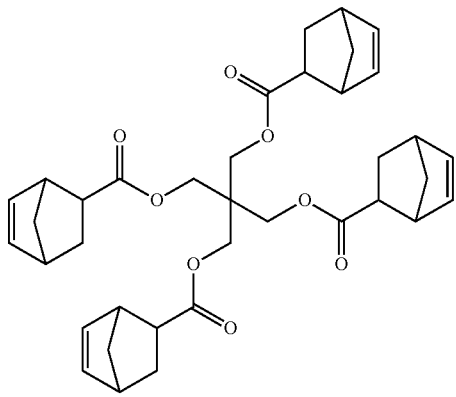

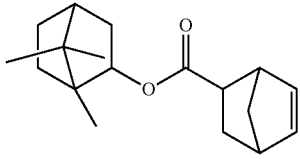
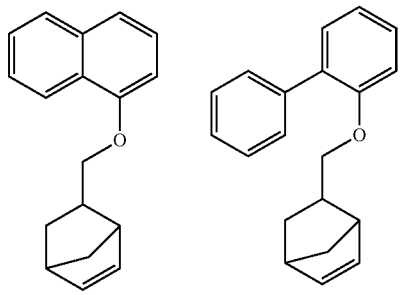

R = $C_2H_5$ to $C_{16}H_{33}$

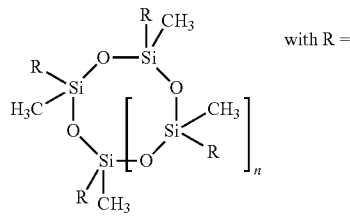

with R =

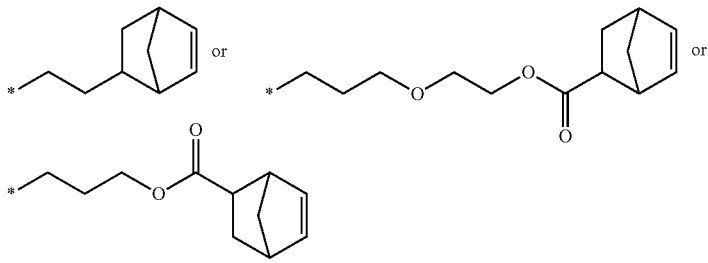

and n=0, 1, 2, 3, 4, 5 or 6.

With any norbornene (bicyclo[2.2.1]hept-5-enyl) group in the preceding formulas the corresponding 7-oxa-norbornene (7-oxa-bicyclo[2.2.1]hept-5-enyl) derivatives are comprised as well. For reason of simplicity stereoisomers at the norbornene moiety are generally not explicitly mentioned in the formulae. It should, however, be understood that all isomers either exo- or endo- to the norbornene ring and mixtures of both are comprised. The two-dimensional formula

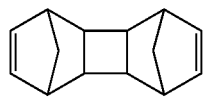 [SMILES: C1=CC2CC1C1C2C2C3C=CC(C3)C12]

therefore refers to any of the following isomers or possible others and mixtures of all of these:

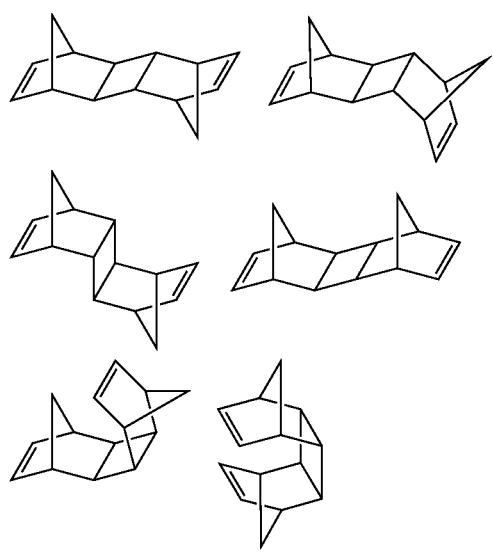

Accordingly, showing one enantiomeric Norbornenyl-Isomer in any case means also the other enantiomer or a mixture of those:

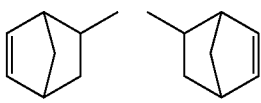

two enantiomers

The bicyclic ring systems listed are easily accessible through the known cyclisation reactions such as e.g. cyclo additions, especially Diels-Alder reactions. They are generally stable and not moisture-sensitive at room temperature and in the presence of conventional dental fillers.

In a preferred embodiment, a composition according to the invention can contain a monomer selected from the group consisting of monomers comprising at least 2 moieties which are polymerizable by ROMP, monomers with at least one moiety selected from the group consisting of cyclobutenyl, cyclopentenyl, cyclooctenyl, norbornenyl and oxa-norbornenyl, monomers with at least one Si-atom, monomers according to the general formula $B(-A)_n$ wherein B is a monomeric oligomeric or polymeric organic or silicon-organic structural element and A is a structural element having at least one functional group which is polymerizable by ROMP and n is 1 to about 10,000 or 5 to about 1,000 or 10 to about 100.

In another embodiment of the invention, the polymerizable matrix composition comprises one or more oligomeric or prepolymeric structures e.g. polyether, polyester or polysiloxane or copolymeric compounds (PDMS) that are tethered and/or end-capped with groups that can undergo a ROMP reaction to form a cured article.

Other useful oligomeric and polymeric monomers are described in the list below
Monomerlist 2:

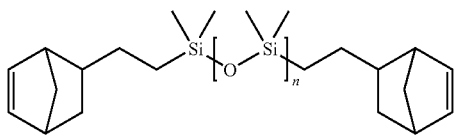

wherein n=1 to about 1,000, e.g. 2 to about 100

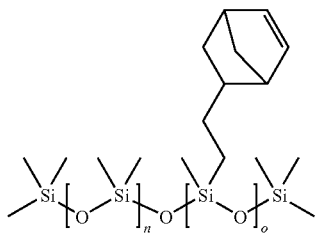

wherein n=1 to about 1,000, for example 2 to about 100; o/n=0.001-1

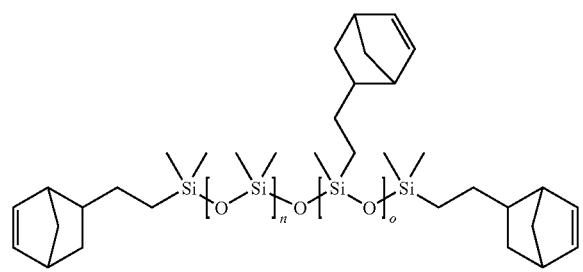

wherein n=1 to about 1,000, for example 2 to about 100; o/n=0.001-1

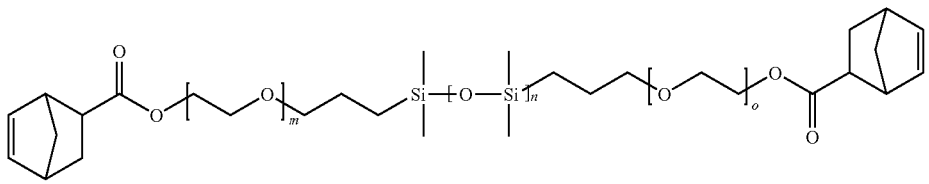

wherein n=1 to about 1,000, e.g. 2 to about 100 and m+o=0 to about 1,000, e.g., 0 to about 100

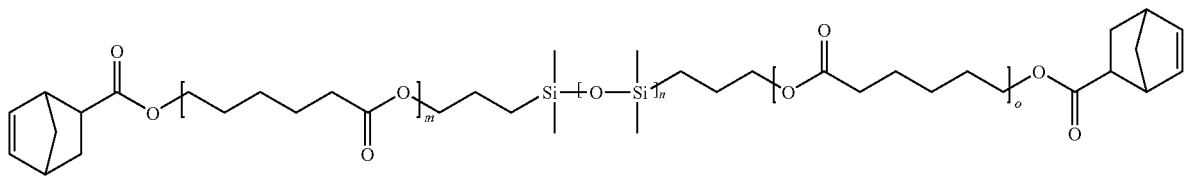

wherein n=1 to about 1,000, e.g., 2 to about 100 and m+o=0 to about 1,000, e.g., 0 to about 100

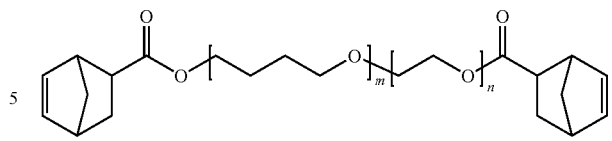

wherein n=1 to about 100, e.g. 2 to about 60 and m/n=1 to about 10; e.g. 1 to 5

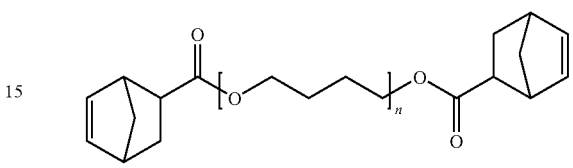

wherein n=1 to about 100, e.g. 2 to about 60

Yet another category of oligomers and/or polymers that may be used in compositions of the invention include tri- or quadrifunctional oligomers or polymers having siloxane backbone end-functionalized or end-capped with an olefin group curable by a metathesis reaction, such as cycloalkenyl groups, for example norbornenyl or norbornenylethyl groups. An example of such polymer is quadrifunctional polydimethyl siloxane (PDMS), end-capped with norbornenyl (NBE) groups.

In addition to the above categories of oligomers and polymers, the resin system may comprise any other polymerizable cycloalkenyl-functionalized siloxane based oligomers or polymers that may undergo polymerization via ROMP mechanism.

Monomers taken from MONOMERLIST 1 may provide beneficial results.

It can also be advantageous if the composition contains at least one monomer with two moieties polymerizable by ROMP and a molecular weight of more than about 180, especially more than about 200 or more than about 250 or more than about 300. The upper limit for the molecular weight is not particularly limited, however, should be in a range where the handling of the composition with regard to its formability is still possible (the composition is not a solid and too viscous to be formed) and the material properties of the cured composition are in a desired range.

The amount of monomer that is curable by ring-opening metathesis polymerization (ROMP), can often vary between about 10 and about 90% by weight. In some cases an amount of about 15 to about 50 or about 20 to about 40% by weight, can lead to good results.

A composition according to the invention also contains at least one initiator of the Hoveyda-Grubbs type for initiating the ROMP. In the context of the invention a Hoveyda-Grubbs Type initiator is defined as a ruthenium carbene complex with an ortho-alky-ether at the benzylidene residue, wherein this ether moiety coordinates to the ruthenium central atom. Preferred Hoveyda-Grubbs type initiators compounds are e.g. listed under CAS-Nos. [301224-40-8], [203714-71-1] or are substituted derivatives thereof.

Generally, all initiators of the Hoveyda-Grubbs type can be used in a composition according to the invention. Thus, either initiators of the Hoveyda-Grubbs I type or of the Hoveyda-Grubbs II type can be used. It is also possible to use mixtures of two or more of Hoveyda-Grubbs I initiators or of Hoveyda-Grubbs II initiators or to mix one or more of Hoveyda-Grubbs I initiators with one or more Hoveyda-Grubbs II initiators according to the invention. It can be preferred if an initiator or a combination of initiators is used which allows for a curing temperature of the composition of below about 60° C., preferably below about 55 or below about 50° C. It can also be advantageous, if the curing temperature is even below about 45° C. or below about 40° C. Possible initiators to be used according to the invention are initiators according to the following formula

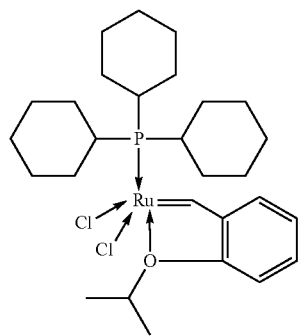

Hoveyda-Grubbs I

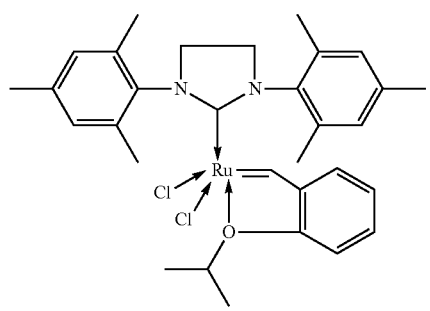

Hoveyda-Grubbs II of which 1,3-bis-(2,4,6-trimethylphenyl)-2-(imidazolidinyliden)dichloro(o-isopropoxy-vinylmethylen)ruthenium can be preferred as an initiator in a composition according to the invention.

An initiator of the Hoveyda-Grubbs type for initiating a ROMP can be present in an amount of about 5 to about 10,000 ppm by weight, or from about 50 to about 6,000 ppm by weight or from about 70 to about 3,000 ppm by weight or about 100 to about 1,000 ppm or about 200 to about 600 ppm, relating to the weight of the entire composition. The inventive composition can comprise one initiator or a mixture of two or more initiators.

If the composition comprises a mixture of two or more initiators, the mixture can consist of initiators only selected from the group of Hoveyda-Grubbs initiators of type I or only of initiators selected from the group consisting of Hoveyda-Grubbs initiators of the type II.

It is, however, also possible that the composition comprises mixtures of one or more initiators of the Hoveyda-Grubbs type I and one or more initiators of the Hoveyda-Grubbs type II. It can be preferred if the composition comprises one, two or three different initiators molecules, especially one or two different initiator molecules.

Suitable initiators of the Hoveyda_Grubbs-Type are also disclosed in US 2003/220512 A (S. Blechert), WO 2005/053843 A (Boehringer Ingelheim GmbH), WO 200214376 A, (Hoveyda et. al), US 2004/254320 A (Kerr Corp.), WO 2004/035596 A (Boehringer Ingelheim GmbH) or DE 10 335 417 A (Arlt), the disclosure of which is expressly mentioned as a source of information with regard to the invention and the disclosure of which is regarded as being a part of the disclosure of the present text.

Besides the above-mentioned monomers and the initiator or initiators a composition according to the invention comprises also a retarder. Generally, a retarder according to the invention is defined as being a compound which, if present, decreases the reaction rate of at least one reaction resulting in a ring opening metathesis polymerization as compared to a composition not comprising the retarder under basically identical conditions. In a more narrow defined definition a retarder according to the invention is a compound which slows down the setting behaviour of a composition comprising the retarder when polymerizing the composition by ROMP. It is also proven to be advantageous, if a retarder aids in keeping the peak reaction temperature of the composition during polymerization below a value of about 60° C., especially below a value of about 50° C.

It can also be desirable, if a retarder is chosen such that the time measured until an onset of the polymerization can be detected via measurement of viscosity increase is retarded as compared to a composition without the retarder under identical conditions. It can be preferred if the time until both compositions are cured, is basically identical.

A retarder which can be used according to the invention is selected from the group consisting of heterocyclic amines having a ring with at least one N-atom and five, four or less atoms constituting the ring bearing at least one N-atom. Compounds exhibiting this characteristic structural element are preferably selected from the group consisting of pyrrole, pyrroline, pyrrolidine, pyrrolidone, porphine, indole, isoindole, carbazole, pyrazole, imidazole, indazole, benzimidazole, oxazole, isoxazole, thiazole, isothiazole, oxazoline, oxazolidine, benzthiazole, 1,2,3- and 1,2,4-triazole, aminotriazole, tetrazole, thiadiazole and their derivatives.

In a further embodiment of the invention the retarder is selected from the group consisting of heterocyclic amines with one, two, three or four N-atoms in a ring with five or less atoms or seven or more atoms constituting the ring.

In a further embodiment of the invention the retarder is selected from the group consisting of pyrrole, imidazole, benzimidazole and triazole.

The retarder is usually neutral in charge, that is, the retarder is usually not of ionic nature.

It has in some instances also been proven to be advantageous if the composition according to the invention comprises more than one type of retarder. Thus, a composition according to the invention can comprise two or more different types of retarders, e.g., two, three or four different types of retarder molecules. However, it has often proven to be successful if only one type of retarder is used.

In another embodiment of the invention the retarder is selected such that it can form a complex with ruthenium. Whether a compound is capable of forming such a complex can, e.g., be determined by NMR measurements.

If a composition according to the invention comprises two or more different types of retarders, it can be sufficient if only one of the retarders is able to form a complex with ruthenium, if such a retarder is desired.

While it is possible to use the above-mentioned heterocyclic compounds as retarders themselves, it can also be advantageous if a composition according to the invention comprises a retarder which has at least one linear or branched aliphatic saturated substituent with about 1 to about 24, especially about 8 to about 18 C-atoms, preferably in N-position. However, other ring positions are also possible. Thus, retarders having two, three or four substituents as described in the text are also included.

Radicals being suitable as respective substituents can, e.g., be selected from the group consisting of capronyl, caprylyl, caprinyl, lauryl, myristyl, palmityl, margaryl, stearyl, arachyl, behenyl or lignoceryl as well as their branched isomers. In a further embodiment of the invention the use of N-caprinylimidazol, N-laurylimidazol, N-myristylimidazol or N-palmitinylimidazol can be preferred.

It can also be preferred if a retarder is used which has a boiling point above about 60° C., especially above about 100° C. or above about 150° C. or above about 200° C. at ambient conditions, i.e., at a pressure of about 1013 mbar.

While generally all types of retarders fulfilling the above conditions can be used, it can be advantageous if a retarder is used which is liquid or which is a soluble solid. If the retarder is a soluble solid the composition should be chosen such that the retarder is soluble in the composition, either due to being soluble in one of the mandatory constituents or due to being soluble in a solvent which can be deliberately added.

In a further embodiment of the invention the retarder can be chosen such that the molar ratio of the retarder or a mixture of two or more retarders to the molar amount of metal atoms in the Hoveyda-Grubbs initiator is from about 10:1 to about 1:15 or about 5:1 to about 1:6.

With regard to the molar ratio of the retarder or a mixture of two or more retarders to the molar amount of metal atoms in the Hoveyda-Grubbs initiator it can be advantageous if the molar ratio is chosen such that the onset of polymerization, as detectable by determination of the curing behaviour, is in a range of from about 30 to about 500 s (seconds) or from about 50 s to about 300 s, especially from about 60 s to about 240 s.

The curing behaviour of the pastes can be determined using a Wallace-Shawburg Curometer as described below. FIG. 1 shows the curing behaviour of an example of the inventive composition determined with such a device.

It has further proven to be successful if the time between the onset of the polymerization and the end of the polymerization is within a range of about 3 min (minutes) to about 7 min especially from about 4 min to about 6 min.

A composition according to the invention can contain the retarder in an amount of about 25 to about 60,000 ppm, based on the weight of the entire composition. In some instances it has proven to be successful if the amount of retarder is about 100 to about 30,000 ppm, or about 200 to about 25,000 ppm or about 300 to about 6,000 ppm each based on the weight of the entire composition.

In a further embodiment of the invention a composition in its polymerized state has a glass transition temperature of more than about 70° C. or more than about 90° C. or more than about 110° C.

In a further embodiment of the invention, the composition comprises one or more additives selected from the group consisting of fillers, stabilizers, opacity modifiers, softeners, compatibilizers, solvents, rheology modifiers, colour pigments or fibers.

The composition to be cured thus also can contain a filler or a mixture of two or more fillers, e.g., organic or inorganic fillers, preferably inorganic fillers. Fillers can be solid materials, e.g., ground inorganic materials like all modifications of $SiO_2$ (e.g. quartz, christobalite) or glasses or precipitated material or material obtained by sol-gel procedures like "chemical ceramics" or organic or inorganic fibres, felts or beads as well as highly dispersed fumed or precipitated fillers ($SiO_2$, $ZrO_2$ or other metal oxides) or nanoshaped spherical or clustered metal oxides which preferably can enhance the mechanical properties of the cured composition. The size of used filler often ranges (but is not limited to) from several microns, down to a few nm.

Preferred particulate fillers can be amorphous materials on the basis of mixed oxides comprising $SiO_2$, $ZrO_2$ and/or $TiO_2$ as are described for example in DE 40 29 230 A1, microfine fillers such as pyrogenic silicic acid or precipitation silicic acid as well a macro- or minifillers such as quartz, glass ceramic or glass powders with an average particle size of about 0.01 to about 5 μm as well as X-ray opaque fillers, such as ytterbium trifluoride. Furthermore glass fibres, polyamide or carbon fibres can be used as fillers.

Preferred fillers can be mixtures of (a) amorphous spherical particles comprising silicon dioxide and up to about 20 mol-% of an oxide of at least one element of the groups I, II, III and IV of the periodic system with a refractive index of about 1.45 to about 1.58 and an average primary particle size of about 10 nm to about 10 μm and (b) quartz, glass ceramic or glass powders or their mixtures with a refractive index of about 1.45 to about 1.58 and an average particle size of about 0.5 to about 5 μm.

A composition to be cured according to the invention can, e.g., contain only one type of filler. It is also possible and can be preferred that a composition to be cured contains two or more different types of fillers. Different types of fillers can differ in chemical constitution, shape, size, size distribution or other features or combinations of two or more of the above mentioned features.

The fillers can be modified by interfacial compounds. Interfacial compounds are substances that chemically link to the surface of fillers, e.g., by condensation, and are able to incorporate into the polymer network produced by ROMP. Usually, they comprise two different functionalities. One functionality is able to chemically bond to the surface of the filler material, the second functionality is able to crosslink with the monomer matrix, normally through a ROMP reaction. Preferred substances are silanes described by the general formula $X_a R_b SiR^1_{(4-a-b)}$, wherein X is hydrogen, halogen, hydroxyl, alkoxy, acyloxy, alkylcarbonyl, alkoxycarbonyl or —NR"$_2$ preferably methoxy or ethoxy; R is alkyl, aryl, alkylaryl or arylalkyl; R" is hydrogen, alkyl or aryl; $R^1$ is an organic group comprising an unsaturated strained cycloaliphatic group that is able to incorporate into a polymeric network obtained by ROMP, preferably norbornenyl, 7-oxa-norbornenyl, cyclobutenyl, cyclopentenyl or cyclooctenyl, a is 1, 2 or 3; b is 0, 1 or 2 and (a+b<4). Preferred examples are:

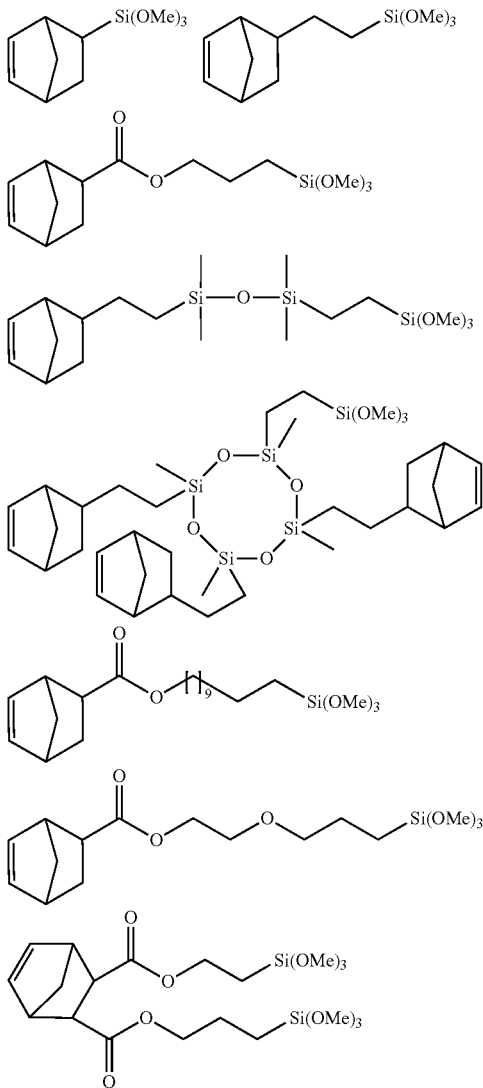

The interfacial compounds can also be used in mixture with such interfacial compounds which chemically link to the surface of fillers, e.g., by condensation, and are not able to be incorporated into the polymer network produced by ROMP. Illustrative examples include MeSi(OMe)$_3$ or C$_6$H$_5$Si(OMe)$_3$.

The compositions to be cured can contain fillers in an amount of about 10 to about 90% by weight, preferably in an amount of about 40 to about 85 or about 60 to about 80% by weight. It can be preferred if the filler contains different compounds, differing with regard to their size, e.g. structural fillers and microfillers. The amount of micro fillers can be 0 to about 50% by weight.

Stabilizers to be optionally part of a composition according to the invention can generally be all stabilizers which do not harm a composition according to the invention. Suitable stabilizers can be organic esters of the phosphoric acid (phosphites) or alkyl or aryl phosphonates or those mentioned by Martin Dexter, Richard W. Thomas and Roswell E. King III, in *Encyclopedia of Polymer Science and Technology* Copyright © 2002 by John Wiley & Sons, Inc.; Vol. 5, 164-183.

A composition to be cured according to the invention can further contain one or more opacity modifiers. As opacity modifiers substances can be used which have a high ability to scatter the light in the matrix, preferably substances which show sufficiently different refractive indices to the rest of the formulation e.g. TiO$_2$, Al$_2$O$_3$, YF$_3$ or YbF$_3$.

Suitable solvents which can be used include water, alcohols like ethanol, acetone or DMSO or mixtures of two or more of these solvents. Ionic liquids are usually not included.

The composition can also contain softeners. Suitable softeners can be aliphatic or branched alkanes of monomeric, oligomeric and polymeric nature which can be hydrocarbons or substituted by oxygene like e.g. poly-THF, PEG, or carbonyls or esters, especially of the following structures:

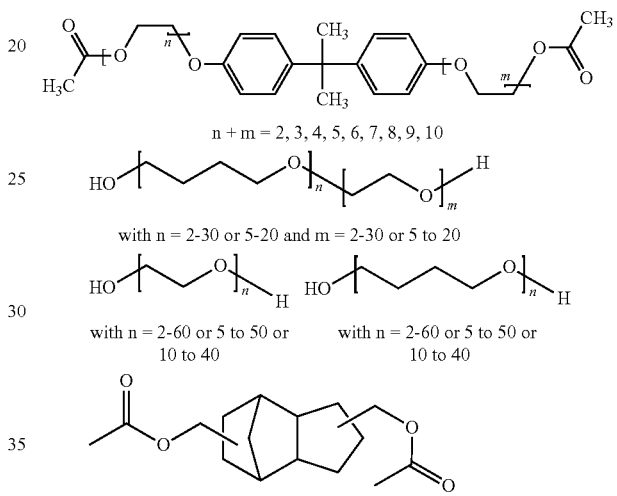

A composition according to the invention can comprise
about 5 to about 85% by weight of fillers,
about 10 to about 85% by weight of one or more monomers polymerizable by ROMP,
about 0 to about 80% by weight of one or more solvents,
about 50 to about 6,000 ppm by weight of at least one initiator of the Hoveyda-Grubbs type for initiating a ROMP
about 10 ppm by weight to about 1% by weight of at least one retarder selected from the group consisting of heterocyclic amines having a ring with at least one N-atom and 5 or less atoms constituting the ring bearing the at least one N-atom and
about 0 to about 70% by weight of one or more additives, with the proviso that the amounts of constituents of the composition add up to 100% by weight.

Certain compositions according to the invention can have one or more of the following features:
the onset time for setting is at least about 0.5 min or at least about 1 min or at least about 1.5 min,
the flexural strength of the cured product is at least about 50 MPa or at least about 60 MPa or at least about 70 MPa (measured according to DIN EN ISO 4049),
the Youngs' Modulus of the cured product is at least about 900 MPa or at least about 1200 MPa or at least about 1500 MPa or at least about 1700 MPa (measured according to DIN EN ISO 4049),
the curing temperature of the composition is below about 60° C.

It has shown to be possible according to the invention that compositions curable by ROMP can be prepared, which can exhibit a tooth-like colour while still allowing for a tailored polymerization behaviour.

A colour classification system which is widely used in the dental field is the VITA™ dental shade guide. A more detailed description of the determination of tooth colours is given by Andres Baltzer and Vanik Kaufmann-Jinoian in Quintessenz Zahntechnik, 30, 7, 726-740 (2004).

It has been found that the cured inventive composition—without containing pigments or other colorants—can have a tooth-like colour appearance. Based on the measured L*a*b values, the colour of the composition can be aligned to the VITA™ colour system as mentioned above. This is possible, e.g. if the L*a*b* values of the inventive composition are in a specific range.

Useful values for "L*" include values higher than or equal to about 55 or 60 or 65. Useful values for "a*" include values below or equal to about 10 or 5 or 0. Useful values for "b*" include values below or equal to about 32 or 28 or 25. Useful values for the opacity include values below or equal to about 98 or 96 or 95.

Composition having L*a*b* values in these ranges can be adjusted to dental colours of the VITA™ colour system by adding e.g. organic colorants or pigments such as carbon black or $TiO_2$.

The composition according to the invention can be provided as a two component system, comprising a base component and a catalyst component. The base component at least comprises one or more monomers polymerizable by ROMP and the catalyst component at least comprises at least one initiator of the Hoveyda-Grubbs type for initiating a ROMP. The retarder is present in the base component or the catalyst component or in both.

Generally, a two component system according to the invention can comprise the necessary constituents in any distribution between the base component and the catalyst component, however, in a preferred embodiment the distribution is such that the above mentioned criteria can be satisfied.

It can, however, be preferred if in a composition according to the invention, the base component at least comprises
  about 5 to about 85 or about 10 to about 80% by weight of one or more fillers,
  about 10 to about 90 or about 15 to about 80% by weight of one or more monomers polymerizable by ROMP,
and the catalyst component at least comprises
  about 10 to about 80 or about 15 to about 70% by weight of one or more fillers
  about 10 to about 80 or about 15 to about 70% by weight of one or more solvents, and
  about 100 to about 2,000 ppm by weight of comprises at least one initiator of the Hoveyda-Grubbs type for initiating a ROMP,
wherein the retarder is present in either the base component or the catalyst component or both, with the proviso that the amounts of constituents of the composition add up to 100% by weight with respect to either the base or catalyst paste.

The invention also relates to a composition obtainable by mixing a base component and a catalyst component, wherein the base component or the catalyst component or both contain at least one retarder selected from the group consisting of heterocyclic amines having a ring with at least one N-atom and 5 or less atoms constituting the ring bearing the at least one N-atom.

The base component and catalyst component can generally be mixed in any ratio desired. It can be preferred due to practical reasons, e.g., due to reasons of distribution of the constituents in the mixed composition or due to the use of mechanical mixing devices, if the catalyst component and the base component are mixed in a weight ratio of about 1:20 to about 1:1 or about 1:10 to about 1:2 or 1:5 to about 1:4.

The invention also relates to a process for the preparation of a composition which is polymerizable by ring-opening metathesis polymerization (ROMP) wherein
  a) at least one monomer that is polymerizable by ROMP and
  b) at least one initiator of the Hoveyda-Grubbs type for initiating the ROMP and
  c) at least one retarder selected from the group consisting of heterocyclic amines having a ring with at least one N-atom and 5 or less atoms constituting the ring bearing the at least one N-atom
are mixed.

In a further embodiment of the process according to the invention, the at least one monomer that is polymerizable by ROMP and the at least one initiator of the Hoveyda-Grubbs type for initiating the ROMP and the at least one retarder selected from the group consisting of heterocyclic amines having a ring with at least one N-atom and 5 or less atoms constituting the ring bearing the at least one N-atom are present in a base component and a catalyst component prior to mixing, and the base component at least comprises one or more monomers polymerizable by ROMP and the catalyst component at least comprises at least one initiator of the Hoveyda-Grubbs type for initiating a ROMP and the retarder is present in the base component or the catalyst component or in both.

In a process according to the invention, the base component can at least comprise
  about 5 to about 85 or about 10 to about 80% by weight of one or more fillers,
  about 10 to about 90 or about 15 to about 80% by weight of one or more monomers polymerizable by ROMP,
and the catalyst component can at least comprise
  about 10 to about 80 or about 15 to about 70% by weight of one or more fillers
  about 10 to about 80 or about 15 to about 70% by weight of one or more solvents, and
  about 100 to about 2,000 ppm by weight of comprises at least one initiator of the Hoveyda-Grubbs type for initiating a ROMP,
wherein the retarder is present in either the base component or the catalyst component or both, with the proviso that the amounts of constituents of the composition add up to 100% by weight with respect to either the base or catalyst paste.

The invention further relates to dental material obtainable by polymerizing a composition according to the invention or by polymerizing a composition obtainable according to a process according to the invention.

The invention also relates to the use of a substance selected from the group consisting of heterocyclic amines having a ring with at least one N-atom and 5 or less atoms constituting the ring bearing the at least one N-atom or of a mixture of two or more of such substances as a retarder in ROMP.

The invention also relates to the use of a material obtainable by polymerizing a composition according to the invention or by polymerizing a composition obtainable according to a process according to the invention for the preparation of temporary or permanent inlays, onlays, veneer shells, crowns, or bridges, impression materials or filling materials.

Especially for dental applications, the retarders used should not lead to a dark coloured and/or bad smelling compositions. As far as possible, the composition should be toxicologically harmless (e.g. showing a negative Ames test).

With respect to certain embodiments of the invention, the curable composition does not contain pyridine or a pyridine structure containing molecule. Typically, with respect to certain embodiments of the invention, there is also no absolute need for the presence of tetra allyl silane (TAS) or tetra allyloxy silane (TAOS).

Thus, with respect to certain embodiments of the invention, the curable composition can essentially be free from pyridine or a pyridine structure containing molecule and/or TAS and/or TAOS.

The invention is further illustrated by examples, the content of which is not intended to limit the scope of the invention.

EXAMPLES

Measurements
L*a*b* Values

The L*a*b* values were determined using a Lab scan (Hunter Lab, USA). The measurement was done either against a white or black coloured background, using 0°/45° measurement angle and 10° as a determination angle.
Flexural Strength Flexural strength and Youngs' Modulus were determined according to DIN EN ISO 4049 using a Zwick Universal Testing Machine (Zwick Company, Ulm, Germany).

Curing Behaviour

The Curometer used for measuring the time for onset ($t_A$) of the curing reaction in the examples was a Wallace-Shawburg Curometer (Croydon, GB).

The Curometer measures the cure time of rubber and other cross linking polymers. It can also measure the setting time of resins, cements and dental impression and filling materials. The Curometer can be used for initial research into stock formulation and also for rapid evaluation of cure for quality control.

The terms "cure" or "vulcanisation" usually refers to the change in a network molecular structure. The Curometer measures the times to beginning of cure and end of cure. The shape of the Curometer curve provides a picture of cure characteristic in which the "delay period" and rate of cure can be seen.

For the measurement of the setting behaviour 1 g base paste and 0.1 g catalyst paste were mixed and placed within 1 min into the measurement area of the Curometer. The Curometer run time is started with the beginning of the mixing. The measurement was conducted at ambient conditions (23° C.). The accuracy of measurement is about +/−0.2 min.
Abbreviations:

Chemical structures and names for the individual components used are:

T-Norbornene:

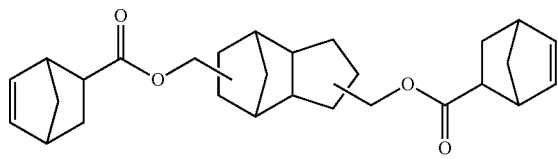

Z-Norbornene:

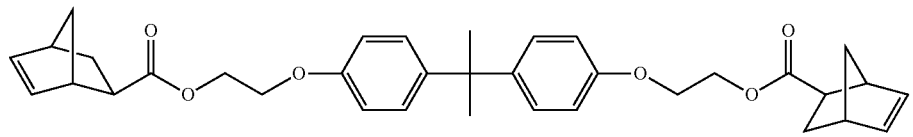

Benozate:

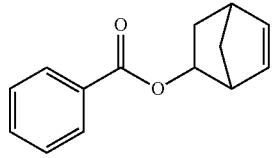

N-Laurylimidazole:

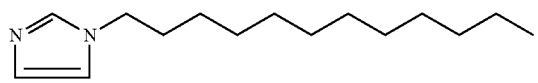

Quarz sil: Quarz, milled to a $D_{50}$ of <1 μm with 5 weight % of 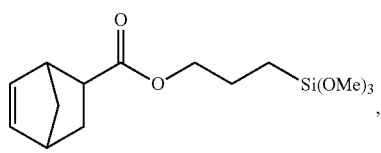, heat treated at 80° C. for 2 h.

Z-Acetate:

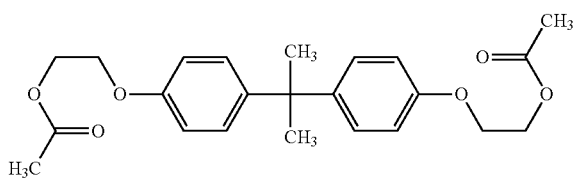

For the following examples the base and catalyst pastes were compounded by mixing the given components into a homogenous paste. The base and catalyst pastes were used after storage for about 1 h at ambient conditions (room temperature, 23° C.).

The base and catalyst pastes were mixed in a ratio of 10:1 (base:catalyst) and the physical parameters curing behaviour, flexural strength, Youngs's Modulus and L*a*b values were determined. The measured values are given below in Tables 1 and 2.

The compositions of the pastes are as given below:
Paste 1—without Retarder (Paste 1):
  Base-paste: 5.000 g Quartz, sil., 2.250 g T-Norbornene, 2.250 g Benzoate, 0.500 g HDK H-2000 (Wacker Company, Germany).
  Catalyst-paste: 0.003 g Hoveyda-Grubbs 2, 0.880 g Z-Acetate, 0.120 g HDK H-2000.
Paste 1—with Retarder (Paste 1 R):
  Base-paste: 5.000 g Quartz, sil., 2.250 g T-Norbornene, 2.250 g Benzoate, 0.500 g HDK H-2000 (Wacker Company, Germany), 0.001 g N-Laurylimidazole (equal to 0.01 mmol).
  Catalyst-paste: 0.003 g Hoveyda-Grubbs 2, 0.880 g Z-Acetate, 0.120 g HDK H-2000.
Paste 1—with TAS (Paste 1TAS):
  Base-paste: 5.000 g Quartz, sil., 2.250 g T-Norbornene, 2.250 g Benzoate, 0.500 g HDK H-2000 (Wacker Company, Germany), 0.002 g tetra allyl silane (TAS) (equal to 0.01 mmol).
  Catalyst-paste: 0.003 g Hoveyda-Grubbs 2, 0.880 g Z-Acetate, 0.120 g HDK H-2000.
Paste 2—without Retarder (Paste 2):
  Base-paste: 5.000 g Quartz, sil., 2.250 g Z-Norbornene, 2.250 g Benzoate, 0.500 g HDK H-2000 (Wacker Company, Germany).
  Catalyst-paste: 0.003 g Hoveyda-Grubbs 2, 0.880 g Z-Acetate, 0.120 g HDK H-2000.
Paste 2—with Retarder (Paste 2R):
  Base-paste: 5.000 g Quartz, sil., 2.250 g Z-Norbornene, 2.250 g Benzoate, 0.500 g HDK H-2000 (Wacker Company, Germany), 0.001 g N-Laurylimidazole.
  Catalyst-paste: 0.003 g Hoveyda-Grubbs 2, 0.880 g Z-Acetate, 0.120 g HDK H-2000.
Paste 3—without Retarder (Paste 3):
  Base-paste: 5.000 g Quartz, sil., 2.250 g Z-Norbornene, 2.250 g Benzoate, 0.500 g HDK H-2000 (Wacker Company, Germany).
  Catalyst-paste: 0.003 g Hoveyda-Grubbs 2, 0.880 g Z-Acetate, 0.120 g HDK H-2000.
Paste 3—with Retarder (Paste 3R):
  Base-paste: 5.000 g Quartz, sil., 2.250 g Z-Norbornene, 2.250 g Benzoate, 0.500 g HDK H-2000 (Wacker Company, Germany), 0.016 g Norbornene-2-yl-methyl-imidazole.
  Catalyst-paste: 0.003 g Hoveyda-Grubbs 2, 0.880 g Z-Acetate, 0.120 g HDK H-2000.
Paste 4—without Retarder (Paste 4):
  Base-paste: 5.000 g Quartz, sil., 2.250 g Z-Norbornene, 2.250 g Benzoate, 0.500 g HDK H-2000 (Wacker Company, Germany).
  Catalyst-paste: 0.003 g Hoveyda-Grubbs 2, 0.880 g Z-Acetate, 0.120 g HDK H-2000.
Paste 4—with Non Retarding Amine (Paste 4R):
  Base-paste: 5.000 g Quartz, sil., 2.250 g Z-Norbornene, 2.250 g Benzoate, 0.500 g HDK H-2000 (Wacker Company, Germany), 0.009 g Triethylamine.
  Catalyst-paste: 0.003 g Hoveyda-Grubbs 2, 0.880 g Z-Acetate, 0.120 g HDK H-2000.

TABLE 1

| | Paste | | |
| --- | --- | --- | --- |
| | 1 | 1TAS | 1R |
| $t_A$ (beginning of cure); [min] | 0.6 | 0.7 | 2.8 |
| Flexural strength; [MPa] | 56.9 | 68.9 | 74.4 |
| Youngs' modulus | 1585 | 1891 | 2137 |
| Background for color measurement | Black | Black | Black |
| a* | 1.09 | −0.69 | −2.09 |
| b* | 7.05 | 9.89 | 3.28 |
| L* | 70.88 | 71.84 | 67.24 |
| Opacity; [%] | 94.46 | 92.81 | 84.62 |

TABLE 2

| | Paste | |
| --- | --- | --- |
| | 2 | 2R |
| $t_A$ (beginning of cure); [min] | 0.60 | 3.00 |
| Flexural strength; [MPa] | 66.0 | 74.8 |
| Youngs' modulus | 1519 | 1949 |
| Background for color measurement | Black | Black |
| a* | −2.52 | −1.68 |
| b* | 4.08 | 3.87 |
| L* | 70.77 | 73.24 |
| Opacity; [%] | 91.55 | 90.35 |

TABLE 3

| | Paste | |
| --- | --- | --- |
| | 3 | 3R |
| $t_A$ (beginning of cure); [min] | 0.60 | 1.10 |
| Flexural strength; [MPa] | 66.0 | 73.7 |
| Youngs' modulus | 1519 | 1970 |
| Background for color measurement | Black | Black |
| a* | −2.52 | −2.35 |
| b* | 4.08 | 4.44 |
| L* | 70.77 | 65.83 |
| Opacity; [%] | 91.55 | 84.19 |

TABLE 4

|  | Paste | |
| --- | --- | --- |
|  | 4 | 4R |
| $t_A$ (beginning of cure); [min] | 0.60 | 0.70 |
| Flexural strength; [MPa] | 66.0 | 71.4 |
| Youngs' modulus | 1519 | 1835 |
| Background for color measurement | Black | Black |
| a* | −2.52 | −3.16 |
| b* | 4.08 | 4.21 |
| L* | 70.77 | 65.03 |
| Opacity; [%] | 91.55 | 86.37 |

The composition of Example 4 does not show a relevant retarding effect, as the measurement of $t_A$ is within the accuracy of measurement.

The composition according to Example 1 has already a tooth-like colour appearance. A further adjustment to a specific colour according to the Vita™ colour shade system can be done by adding organic colourants or pigments.

This can be further illustrated with the values given in Table 5 below. As an example the L*a*b values for the shade A3 of the Vita™ colour shade system measured against a black background are given in Table 5.

TABLE 5

| Lab values for colour of the Vita ™ system, shade A3 | |
| --- | --- |
| a* | 2.90 |
| b* | 20.80 |
| L* | 67.50 |
| Opacity; [%] | 91.70 |

An adjustment to a specific shade is usually possible, if the measured L*a*b values are in a certain range. E.g., the formulations described above (Pastes 1R and 2R) can be adjusted to an A3 shade in view of the fact, that the a- and b-values of the pastes are below the a- and b-values measured for the A3 shade. Likewise can be done if the L-value of the new formulation is higher than the one of a specific shade of the Vita™ colour shade system. In this case, a pigment such as carbon black lowering the L-value can be added.

The invention claimed is:

1. A composition which is polymerizable by ring-opening metathesis polymerization (ROMP) comprising:
   a) a monomer that is polymerizable by ROMP;
   b) an initiator of the Hoveyda-Grubbs type for initiating the ROMP; and
   c) a retarder selected from the group consisting of heterocyclic amines having a ring with at least one N-atom and 4 or less other atoms constituting the ring bearing the at least one N-atom, and wherein the retarder comprises at least one linear or branched aliphatic saturated substituent with 1 to 24 C-atoms in N-position.

2. The composition of claim 1, wherein the retarder is able to form a complex with Ru.

3. The composition of claim 1, wherein a molar ratio of the retarder or a mixture of two or more retarders to metal atoms in the Hoveyda Grubbs initiator is about 10 : 1 to about 1 : 15.

4. The composition of claim 1, wherein the retarder is present in an amount of about 10 to about 30,000 ppm, based on the weight of the polymerizable composition.

5. The composition of claim 1, wherein the monomer which is polymerizable by ROMP comprises at least one C-C double bond in a cyclic structure.

6. The composition of claim 1, wherein the monomer is selected from the group consisting of monomers comprising at least 2 moieties which are polymerizable by ROMP, monomers with at least one moiety selected from the group consisting of cyclobutenyl, cyclopentenyl, cyclooctenyl, norbornenyl and oxa-norbornenyl, monomers with at least one Si-atom, and monomers according to the general formula $$B(-A)_n$$

wherein B is a monomeric oligomeric or polymeric organic or silicon-organic structural element and A is a structural element having at least one functional group which is polymerizable by ROMP and n is 1 to about 10000.

7. The composition of claim 1, wherein the ROMP product has a glass transition temperature of more than about 60° C.

8. The composition of claim 1, further comprising one or more additives selected from the group consisting of fillers, stabilizers, opacity modifiers, softeners, compatibilizers, solvents, rheology modifiers, color pigments or fibers.

9. The composition of claim 1, wherein the polymerizable composition comprises:
   about 5 to about 85% by weight of fillers,
   about 10 to about 85% by weight of one or more monomers polymerizable by ROMP,
   about 0 to about 80% by weight of one or more solvents,
   about 50 to about 6,000 ppm by weight of at least one initiator of the Hoveyda-Grubbs type for initiating a ROMP,
   about 10 ppm by weight to about 1% by weight of at least one retarder selected from the group consisting of primary linear or branched aliphatic amines with 1 to 28 C-atoms, primary cycloaliphatic or primary aromatic amines with 5 to 28 C-atoms or heterocyclic amines having a ring with at least one N-atom; and 5 or less atoms constituting the ring bearing the at least one N-atom and
   about 0 to about 70% by weight of one or more additives, with the proviso that the amounts of constituents of the composition add up to 100% by weight.

10. The composition of claim 1, wherein the composition has one or more of the following features:
    an onset time for setting of at least about 30 seconds,
    the flexural strength of the cured composition is at least about 50 MPa,
    the Youngs Modulus of the cured composition is at least about 900 MPa,
    the curing temperature of the composition is below about 60° C.

11. The composition of claim 1, wherein the ROMP product has L*a*b* values that fulfil at least one of the following requirements:
    for "L*": higher than or equal to about 55;
    for "a*": below or equal to about 10;
    for "b*": below or equal to about 32;
    for opacity: below 98.

12. A method of making a dental material, the method comprising mixing a composition according to claim 1 to provide a mixture; and
    subjecting the mixture to ROMP to produce the dental material;
    wherein the dental material is suitable for use in a human oral environment.

13. The composition of claim 1, wherein the initiator of the Hoveyda-Grubbs type is selected from the group consisting of:

a compound of the formula

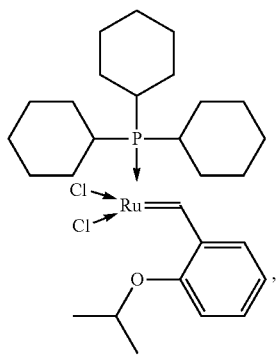

a compound of the formula

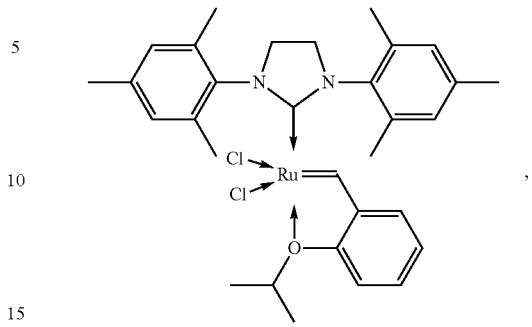

and combinations thereof.

14. A dental material prepared according to the method of claim 12.

15. An article comprising the dental material of claim 14, wherein the article is any of a temporary inlay, a permanent inlay, a veneer shell, a crown, a bridge, an impression material, or a filling material.

* * * * *

UNITED STATES PATENT AND TRADEMARK OFFICE
CERTIFICATE OF CORRECTION

PATENT NO.       : 8,431,625 B2
APPLICATION NO.  : 12/517727
DATED            : April 30, 2013
INVENTOR(S)      : Thomas Luchterhandt et al.

It is certified that error appears in the above-identified patent and that said Letters Patent is hereby corrected as shown below:

On the Title Page, in Column 2, under item (56), "(Other Publications)"
Line 10, delete "Chemistr;" and insert -- Chemistry; --, therefor.
Line 16, delete "Matathesis" and insert -- Metathesis --, therefor.

In the Specification
Column 1
Line 12, delete "Dec. 10," and insert -- Dec. 20, --, therefor.
Line 13, after "herein" insert -- . --.

Column 6
Line 30, delete "ethan" and insert -- ethane --, therefor.

Column 14
Line 20, after "60" insert -- . --.

Column 15
Line 10, delete "alky" and insert -- alkyl --, therefor.
Line 65, delete "methylen" and insert -- methylene --, therefor.

Column 16
Line 20, delete "Hoveyda_Grubbs" and insert -- Hoveyda-Grubbs --, therefor.
Line 59, delete "benzthiazole," and insert -- benzothiazole, --, therefor.

Column 18
Line 18, delete "christobalite" and insert -- cristobalite --, therefor.

Column 25
Line 20, delete "Youngs's" and insert -- Young's --, therefor.

Signed and Sealed this
Thirtieth Day of July, 2013

Teresa Stanek Rea
*Acting Director of the United States Patent and Trademark Office*